United States Patent [19]
Morisaki et al.

[11] Patent Number: 5,763,687
[45] Date of Patent: Jun. 9, 1998

[54] PREPARATION PROCESS FOR AROMATIC MONONITRO COMPOUNDS

[75] Inventors: Jyoji Morisaki, Arao; Masaaki Iijima, Ohmuta; Kouki Oogaki, Fukuoka-ken; Hiroaki Matsuno, Tamana; Takashi Yamaguchi, Ohmuta; Katsuharu Miyata, Sakai, all of Japan

[73] Assignee: Mitsui Chemicals, Inc., Chiyoda-ku, Japan

[21] Appl. No.: 763,146

[22] Filed: Dec. 10, 1996

[51] Int. Cl.$^6$ .................. C07C 205/00; C07C 201/00
[52] U.S. Cl. .................. 568/927; 568/924; 568/928
[58] Field of Search .................. 568/924, 927, 568/928, 932, 937, 939

[56] References Cited

U.S. PATENT DOCUMENTS 3,160,669  12/1964  Terao et al. .

FOREIGN PATENT DOCUMENTS 4410417  8/1995  Germany .

*Primary Examiner*—Gary Geist
*Assistant Examiner*—Karl J. Puttlitz, Jr.
*Attorney, Agent, or Firm*—Burns, Doane, Swecker & Mathis, L.L.P.

[57] ABSTRACT

An improved preparation process for an aromatic mononitro compound comprising reacting an aromatic compound with mixed acid consisting of nitric acid, sulfuric acid or phosphoric acid and water, wherein these flow to react with each other in a reactor comprising a tube inside of which more than one twisted tabular members are aligned in sequence in a manner that a front margin of a twisted tabular member is substantially perpendicular to an back margin of the preceding member, can resolve a number of problems such as an inadequate mixing efficiency, reduction of a reaction rate, associated voluminal increase/complication of a reactor and difficulty in securing safety as well as provide the aromatic mononitro compound with minimal amount of by-products in a considerably short period.

7 Claims, 1 Drawing Sheet

PREPARATION PROCESS FOR AROMATIC MONONITRO COMPOUNDS

BACKGROUND OF THE INVENTION

1. Field of the Invention

This invention relates to a preparation process for an aromatic mononitro compound, comprising nitration of an aromatic compound with mixed acid containing nitric acid. In particular, this invention relates to a preparation process for an aromatic mononitro compound in a reactor with a particular structure.

Aromatic mononitro compounds are industrially useful as dyes, pigments, raw materials for industrial reagents and intermediates as well as raw materials for polymers such as polyamides and urethanes via their reduction to aromatic amines.

2. Description of the Related Art

A variety of preparation processes for aromatic mononitro compounds have been well-known over the years. In the case of nitrobenzene, it is industrially prepared by reacting benzene with a mixture of nitric acid, sulfuric acid and water, called 'mixed acid', in a batch process or in a continuous process, usually controlling the temperature between 60° and 70° C. by removal of its reaction heat. In that case, the mixed acid used initially contains nitric acid at a high concentration of 20 to 30%, in which the ratio of the mixed acid to benzene is usually 3 to 4:1. Acid which has been used contains substantially no nitric acid, and in general becomes a waste fluid of 70% sulfuric acid which is then concentrated to 93 to 95% to be reused. This process has the disadvantages of a large amount of cooling needed for the removal of reaction heat and a large amount of utilities required for concentrating the waste acid so that it can be reused.

In U.S. Pat. No. 2,256,999, a sort of adiabatic process called the 'Castner method' is suggested, wherein used hot acid is concentrated to be effectively reused, by means of a method such as flash distillation, while a major part of the heat generated from mixing and reaction is not dispersed but utilized to accelerate the reaction. Mixed acid in the Castner method is a mixture of 75% sulfuric acid and 63% nitric acid, in which the concentration of the latter is below 10%, specifically 3%. The reaction is carried out at an initial temperature of about 90° C., dropping benzene into a stirring-tank type of reactor.

This method has disadvantages such as those below, due to which the Castner method has failed to be industrially successful.

(1) The reaction mixture is held for a long period in a reactor.

(2) It is difficult to control the reaction.

(3) The system readily reaches an extremely high temperature.

(4) By-products such as dinitrobenzenes are readily formed.

(5) Due to presence of a gas phase in a reactor, reaction readily becomes dangerous.

Later, in JP-B-61-20534 and JP-A-54-32424, Alexander et al. have suggested preparation processes for nitrobenzene, which are modified Castner methods, based on an adiabatic process. In both processes, there are some restraints in reaction conditions, specifically the composition of a mixed acid being 1 to 8.5% of nitric acid, 60 to 70% of sulfuric acid and over 25% of water. They describe that dinitrobenzenes as by-products can be controlled below 500 ppm by carrying out a reaction under such conditions. Furthermore, they describe that 'vigorous stirring' is necessary to disperse benzene and have described the use of a stirring-tank type of reactor in both cases.

In a mixing process using a stirring-tank, a gas phase is essentially formed. In a system in which nitric acid is present, e.g., that of nitration, presence of a gas phase containing organic compounds such as benzene is undesirable because the system has danger such as explosion. Thus, in a system in which nitric acid is present, an apparatus which minimizes a gas phase as much as possible is desirable.

Furthermore, the reaction temperature inevitably rises under adiabatic reaction conditions and long exposure of reactants to a high temperature is not preferable because the longer the exposure is, the more undesirable by-products are formed. When an aromatic mononitro compound is produced in an adiabatic reaction process, the reaction should be, therefore, accelerated as much as possible, to quickly complete the reaction.

Another preparation process for an aromatic nitro compound has been suggested in U.S. Pat. No. 4,973,770, wherein a stream of mixed acid or benzene is atomized into drops with a diameter of below 10 microns through an atomizing nozzle or an equivalent orifice and a turbulent jet stream of the fine drops is passed into the other stream to accelerate a reaction producing nitrobenzene. Even in this process, however, the reactivity was only about 55% with a retention time of approximately 3 minutes, suggesting that it may take over 6 minutes to complete the reaction.

Another process has been suggested in U.S. Pat. No. 5,313,009, wherein nitration is carried out in a circular reactor, using a mixed acid having a particular range of composition (3% or less of nitric acid concentration) where nitric acid contained can be completely dissociated into nitronium ion.

Furthermore, a preparation process for halogenated nitrobenzenes through adiabatic nitration with a particular composition of mixed acid has been disclosed in U.S. Pat. No. 4,453,027.

Furthermore, an adiabatic nitration process of toluene or chlorobenzene has been recently disclosed in JP-A-7-258173 and JP-A-7-278062, which describes that a certain range of mixing energy should be applied as a stirring power to vigorously mix reactants.

These processes, however, have a problem that the structure of the reactor and a reaction path have become complicated.

SUMMARY OF THE INVENTION

The present invention provides an improved process for aromatic mononitro compounds, which can resolve the above problems of conventional techniques such as reduction of reaction rate, increased volume of a reactor, complication of a reactor and difficulty in ensuring safety, and which is carried out very quickly with less by-products.

The present invention comprises the following aspects:

(1) a preparation process for an aromatic mononitro compound, characterized in that mixed acid containing nitric acid and an aromatic compound flow to react with each other in a reactor comprising a tube inside of which more than one twisted tabular members are aligned in sequence in a manner that a front margin of one twisted tabular member is substantially perpendicular to a back margin of the preceding member;

(2) a process according to (1), wherein the reactor consists of the tube and a hollow tube without the tabular members therein;

(3) a process according to (1) or (2), wherein the twisted tabular members are made from ceramics;

(4) a process according to (1) or (2), wherein the reaction temperature in the reactor is below 160° C.;

(5) a process according to (1) or (2), wherein the mixed acid has a composition of 1 to 10% by weight of nitric acid, 20 to 40% by weight of water and the remainder of sulfuric acid and/or phosphoric acid;

(6) a process according to (1) or (2), wherein a fluid in the reactor has a linear velocity of 20 to 300 cm/sec;

(7) a process according to (1) or (2), wherein the aromatic compound is selected from the group consisting of benzene, toluene, chlorobenzene, naphthalene or anthraquinone;

(8) a process according to (1) or (2), wherein a reaction mixture discharged from the reactor is separated into an acid phase and an organic phase; then the acid phase is subjected to flash evaporation to adjust its concentration; and then the resulting acid phase is returned to the reactor to further react.

A process of the present invention can safely and adiabatically carry out nitration of an aromatic compound at a considerably higher reaction rate with a simpler apparatus to give an aromatic mononitro compound with high quality and with a minimal amount of by-products than any of the conventional processes.

DETAILED DESCRIPTION OF THE PREFERRED EMBODIMENTS

Figure 1:
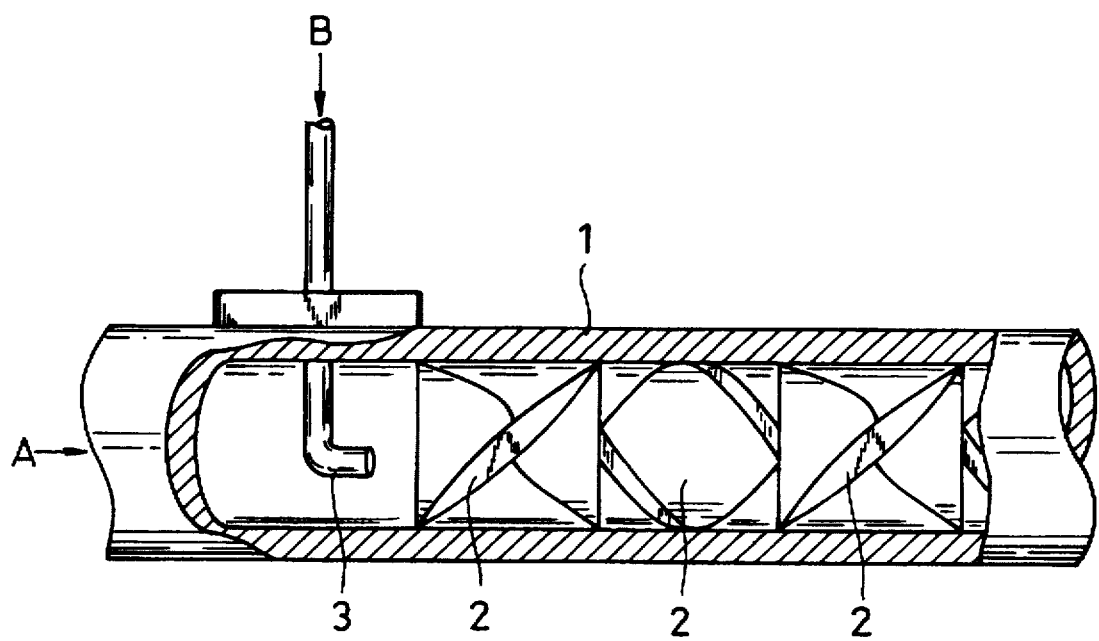
FIG. 1 is a descriptive figure showing an example of a continuous reactor used in a process of the present invention, a part of which is broken to show inside of a mixer tube.
Figure 2:
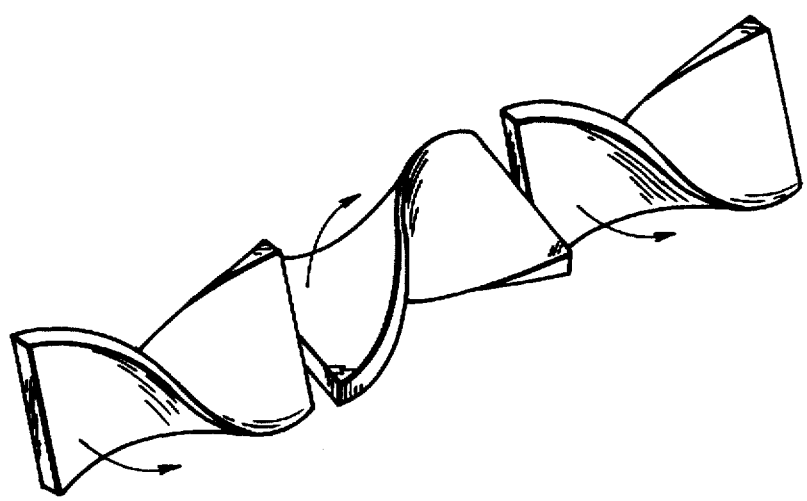
FIG. 2 is a view of several twisted tabular members which are located in the mixer tube of FIG. 1.

In the present invention, a reactor includes a special shape of tube, which is described with reference to the drawings. In FIG. 1, a hollow tube 1 with a round section is a mixer tube for reacting mixed acid with an aromatic compound. Inside of the tube 1, more than one twisted tabular members 2 are aligned in series. In FIG. 1, a part of the tube 1 is broken to show that in its inside there can be seen several tabular members 2. The number of these member 2 can be arbitrarily selected, which will be discussed later. Each of these tabular members 2 has a width almost equal to the internal diameter of the tube 1, and is made of a tabular material whose length is several times longer than its width. Each tabular member 2 is twisted and its front and back margins form a certain angle, preferably within the range of 60° to 210°. Furthermore, each tabular member 2 is preferably twisted to a direction opposite to that of the preceding one, and adjacent margins of two tabular members form a certain angle, preferably 90°. Alternatively, instead of having the twisting directions of adjacent two members opposite, it is possible that a group of several tabular members 2 with the same twisting direction is followed by a group with opposite twisting direction. The tabular members are, therefore, aligned in a manner that groups of right-twisted and left-twisted members are alternately placed, wherein each group consists of one or more tabular members 2.

Since strong acid such as sulfuric acid is used at a elevated temperature in an adiabatic nitration process, the tabular member is preferably made from ceramics, e.g., alumina, zirconia, mullite, silicon carbide, adequately corrosion-resistant to strong Acids such as sulfuric acid, rather than ordinary metal which is inadequately corrosion-resistant.

A tube having the above shape and functions as an apparatus for mainly mixing highly viscous materials is, for example, described in the name of Kenics static mixer in Perry & Chilton, "Chemical Engineers, Handbook", McGraw-Hill, 6th Edition, pp. 19–22. In Japan, it is available from Noritake Company as 'Noritake Static Mixer'. In this type of mixer, fluid is mixed via three kinds of action, i.e., dividing, reversing and turning.

Particularly when used in an adiabatic nitration reaction, this type of mixer has a number of advantages such as listed below, compared with conventional mixing measures such as a mechanical stirrer or other type of non-driven mixer, e.g., 'Sulzer static mixer', Koch Engineering Co., Inc.;

(1) Its simple structure does not lead to formation of dead space and thus pressure loss is minimal.

(2) Reaction can be readily scaled up.

(3) Its maintenance is easy.

(4) A reaction system is readily stabilized or simplified.

(5) Special acid-resistant materials such as ceramics can be used.

(6) Since it has no actuator, it does not generate noise, vibration or troubles of an actuator.

(7) It is safe because it generates substantially no gas phase in a reaction region.

An aromatic compound and mixed acid are simultaneously pumped into the tube. Since when flow rates are significantly different between the aromatic compound and the mixed acid it becomes difficult to homogeneously forward the two solutions into the tube, it is preferable to fit a guide tube 3 as illustrated in FIG. 1 to a tube lower in flow rate. The outlet of the guide tube 3 is on an extension line of the center of the tube inlet, and the diameter of the guide tube 3 is less than that of the tube 1. The smaller the diameter of the guide tube 3 is, the higher the linear velocity is and thus the more the mixing state is improved, while the higher a required pressure resistance is. Thus, the diameter of the guide tube 3 is preferably equal to or more than 2 mm. In an adiabatic nitration reaction, it is preferable to fit a guide tube regardless of the flow rate. In general, a guide tube 3 is fitted to a delivery line for an aromatic compound (B) as illustrated in FIG. 1.

An aromatic compound which can be used in the present invention is any of aromatic compounds which are stable in the presence of hot sulfuric acid and/or hot phosphoric acid; are liquefiable in a temperature range of about 40° to 80° C.; and their nitration products are also stable in the presence of hot aqueous solutions of sulfuric acid and/or phosphoric acid, e.g., benzene, toluene, chlorobenzene, naphthalene and anthraquinone.

The tube 1 filled with tabular members 2 has a region where fine drops of an aromatic compound having passed through a certain number of tabular members 2 can be no longer atomized. The critical number of the member 2 is usually 50 or less, sometimes 20 to 30 or less. An adiabatic nitration reaction proceeds to be completed in this region. Immediately after atomization, the reaction can be maintained within a certain period even in a hollow pipe without tabular members. The reactor may be, therefore, a combination of alternately aligned tubes filled with tabular members and glass-lined hollow-tubes. Such a reactor comprising a combination of tubes and hollow tubes can complete a reaction with less number of tubes than one consisting of only tubes, and can reduce pressure loss with almost the same size of the reactor as a reactor consisting of tubes. Length of a hollow tube corresponds to that of 40 or less, sometimes 20 or less tabular members.

Since a process of this invention is carried out in an adiabatic system, heat from reaction and mixing, and therefore rise of temperature depend on conditions relevant to supplying raw materials such as a composition of mixed acid and a molar ratio of an aromatic compound to nitric acid as well as reaction quantity depending on such conditions. For conditions relevant to supplying raw materials, a variety of combinations are possible although it is preferable to choose those which do not raise the temperature in the system over 160° C. in the light of safety and control of by-products. Concentration of nitric acid in the mixed acid is usually 1 to 10%, preferably 1 to 8%. Concentrations of the other components, i.e., sulfuric acid or phosphoric acid and water can vary to some extent within a range where a temperature of the system does not rise over 160° C. To maintain a temperature of the system below 160° C., the composition preferably consists of 50 to 75%, preferably 55 to 70% of sulfuric acid or phosphoric acid and 20 to 40% preferably 28 to 37% of water. Particularly in the case of nitration of chlorobenzene, it is possible to control an isomer ratio between aromatic nitro compounds, using concentrated phosphoric acid of 74 to 80% estimated as $P_2O_5$ or sulfuric acid as appropriate. Flows of such mixed acid and an stoichiometrically excessive aromatic compound are mixed in static mixers. Reaction is typically initiated at 50° to 100° C. and reach 130° to 150° C.

An aromatic compound is preferably supplied at one or more molar ratio to nitric acid in the mixed acid. Although reaction can be carried out at a molar ratio of less than one, it is problematic in safety. The aromatic compound is usually supplied at a molar ratio of 1 to 3 to nitric acid.

Next, flow rate of a reaction fluid will be described. Since an optimal flow rate of reactants depends on various factors such as size of the reactor and reaction conditions, it cannot be generalized, but in the case of a mixer tube with an inside diameter of 10 to 150 mm, a linear velocity in its tube is usually 20 to 300 cm/sec, preferably 50 to 150 cm/sec. Reaction rate tends to decrease at a linear velocity of less than 20 cm/sec. It is possible to carry out the reaction at a linear velocity of over 300 cm/sec although it will lead to economical problems; e.g., since an optimal size of fine drops has certain limits, applying excessive energy only increases energy loss and a pump, pipes and apparatuses highly resistant to pressure are needed.

Retention time of fluid in a reactor depends on reaction conditions, but it is usually 0.1 second to 5 minutes. Thus, a process of this invention can complete the reaction much more quickly than any of conventional processes, and minimizes by-products.

A reaction mixture discharged from the reactor is separated into an organic phase and an acid phase in a separator. It is recommended that the inside of the reactor is pressurized to prevent both an organic and an acid phases from being flash-evaporated. Since as the pressure also increases a pressure at the inlet of the tube, the pressure in the separator is usually adjusted to 2 to 5 kg/cm²G, preferably 2 to 3 kg/cm²G. The separated acid phase is re-concentrated by a well-known means, e.g., a vacuum flash evaporator utilizing heat generated by reaction and mixing, and is, if necessary, reused. From the organic phase, a desired aromatic nitro compound can be purified by removing impurities contained by use of procedures which are ordinarily conducted in a nitration of an aromatic compound, e.g., washing and distillation.

The following examples specifically illustrate a process of the present invention.

EXAMPLE 1

A reactor consisted of a series of 45 pieces of ceramic Noritake Static Mixers (Model CSM-12-5) with an inside diameter of 12 mm, each of which had eight pieces of ceramic tabular members, i.e., rectangular plates alternately right- or left-twisted by 180°. To the reactor are continuously pumped benzene (hereinafter referred to as Bz) at 24° C. at the rate of 52 kg/h and mixed acid at 99° C. consisting of 65% by weight of sulfuric acid, 5.2% by weight of nitric acid and 29.8% by weight of water at the rate of 570 kg/h, and they were adiabatically reacted. Under these conditions, a molar ratio of Bz/nitric acid was 1.4, a linear velocity in the static mixer was 1.05 m/sec, and a retention time in 24th static mixer was 2.6 sec and 45th static mixer was 4.8 sec. In a steady state one hour after initiation of the reaction, an inlet temperature was 94° C. and an outlet temperature was 148° C. Analyses of acid phases of reaction solutions sampled at the 25th and the 45th static mixers indicated that reactivity of nitric acid to input of nitric acid were 73.0% and 99.8%, respectively. Analysis of the organic phase sampled at the 45th mixer indicated that ratios of by-products to the desired product, nitrobenzene, were 300 ppm for dinitrobenzenes (DNBs), 1500 ppm for dinitrophenols (DNPS) and 200 ppm for trinitrophenols (TNPs).

EXAMPLE 2

The procedure as described in Example 1 was carried out, except that a reactor consisted of a series of 40 pieces of ceramic Noritake Static Mixers (Model CSM-30-5) with an inside diameter of 30 mm, each of which had four pieces of tabular members and that flow rates of mixed acid and Bz were altered to maintain a linear velocity of 1.05 m/sec in the mixer. Under these conditions, a retention time through 40 static mixers was 5.1 sec. In a steady state one hour after initiation of the reaction, an inlet temperature was 94° C. and an outlet temperature was 140° C. Analyses of acid phases of reaction solutions sampled at the 4th, the 5th, the 7th and the 40th static mixers indicated that reactivity of nitric acid to input of nitric acid were 31% , 32%, 33% and 90%, respectively. Analysis of the organic phase sampled at the 40th mixer indicated that ratios of by-products to nitrobenzene, were 260 ppm for DNBS, 1400 ppm for DNPs and 150 ppm for TNPS.

EXAMPLE 3

The procedure as described in Example 2 was carried out, except that a composition of mixed acid was altered to 65.8% by weight of sulfuric acid, 4.0% by weight of nitric acid and 30.2% by weight of water and that a flow rate of mixed acid was 3660 kg/hr and a flow rate of Bz was 254 kg/hr to maintain a linear velocity of 1.05 m/sec in the mixer. Analysis of an acid phase of a reaction solution sampled at the outlet indicated that reactivity of nitric acid to input of nitric acid was 95%. Analysis of its organic phase indicated that ratios of by-products to nitrobenzene were 300 ppm for DNBs, 950 ppm for DNPs and 70 ppm for TNPs.

EXAMPLE 4

The procedure as described in Example 3 was carried out, except that a flow rate of mixed acid was 1400 kg/hr and a flow rate of Bz was 97 kg/hr to maintain a linear velocity of 0.4 m/sec in the static mixer. Under these conditions, a retention time through 40 static mixers was 13.2 sec. Analysis of an acid phase of a reaction solution sampled at the outlet indicated that reactivity of nitric acid to input of nitric acid was 70%. Analysis of its organic phase indicated that ratios of by-products to nitrobenzene were 260 ppm for DNBs, 700 ppm for DNPs and 50 ppm for TNPS.

EXAMPLE 5

The procedure as described in Example 3 was carried out, except that an initial reaction temperature was 120° C. In a steady state after one hour, an outlet temperature was 155° C. Analysis of an acid phase of a reaction solution sampled at the outlet indicated that reactivity of nitric acid to input of nitric acid was 99.8%. Analysis of its organic phase indicated that ratios of by-products to nitrobenzene were 945 ppm for DNBs, 2580 ppm for DNPs and 450 ppm for TNPs.

EXAMPLE 6

A reactor used consistent of series of 23 combinations of two pieces of ceramic Noritake Static Mixers (Model CSM-12-5) with an inside diameter of 12 mm, each of which had eight pieces of tabular members, and a glass-lined hollow tube with an inside diameter of 12 mm and a length of 300 mm. To the reactor are continuously pumped Bz at 24° C. at the rate of 51 kg/h and mixed acid at 99° C. consisting of 65% by weight of sulfuric acid, 5.2% by weight of nitric acid and 29.8% by weight of water at the rate of 565 kg/h, and they were adiabatically reacted. Under these conditions, retention times in a static mixer and a hollow tube were 2.6 sec and 8.8 sec, respectively. Analysis of an acid phase of a reaction solution sampled at the outlet indicated that reactivity of nitric acid to input of nitric acid was 87%. Analysis of its organic phase indicated that ratios of by-products to nitrobenzene were 270 ppm for DNBs, 1200 ppm for DNPs and 100 ppm for TNPs.

EXAMPLE 7

The procedure as described in Example 6 was carried out, except that a length of a glass-lined hollow tube was 800 mm. Under these conditions, retention times in a static mixer and a hollow tube were 2.6 sec and 23.4 sec, respectively. Analysis of an acid phase of a reaction solution sampled at the outlet indicated that reactivity of nitric acid to input of nitric acid was 99.6%. Analysis of its organic phase indicated that ratios of by-products to nitrobenzene were 300 ppm for DNBs, 1500 ppm for DNPs and 200 ppm for TNPs.

EXAMPLE 8

The procedure as described in Example 1 was carried out, except that chlorobenzene at 24° C. was continuously pumped at the rate of 144 kg/h and mixed acid consisting of 70% by weight as $P_2O_5$ of phosphoric acid, 5.2% by weight of nitric acid and 24.8 by weight of water at the rate of 517 kg/h. Under these conditions, a molar ratio of chlorobenzene/nitric acid was 3, a linear velocity in a static mixer was 1.0 m/sec, and a retention time in a static mixer was 2.5 sec. In a steady state one hour after initiation of the reaction, an inlet temperature was 94° C. and an outlet temperature was 135° C. Analysis of an acid phase of a reaction solution sampled at the outlet indicated that reactivity of nitric acid to input of nitric acid was 99%, and that an isomer ratio of chloro-p-nitrobenzene/chloro-o-nitrobenzene (P/O ratio) was 1.15. Analysis of its organic phase indicated that ratios of by-products to chloronitrobenzenes were 1000 ppm for chlorodinitrobenzenes (DNCBS) and 400 ppm for chlorophenols (CPs).

EXAMPLE 9

The procedure as described in Example 8 was carried out, except that mixed acid consisted of 62% by weight of sulfuric acid, 5.2% by weight of nitric acid and 32.8% by weight of water. Under these conditions, analysis of an acid phase of a reaction solution sampled at the outlet indicated that reactivity of nitric acid to input of nitric acid was 50%, and that P/O ratio was 1.66. Analysis of its organic phase indicated that ratios of by-products to chloronitrobenzenes were 600 ppm for DNCBs and 240 ppm for CPs.

EXAMPLE 10

The procedure as described Example 1 was carried out, except that toluene at 20° C. and mixed acid at 90° C. consisting of 70% by weight as $P_2O_5$ of phosphoric acid, 4.5% by weight of nitric acid and 25.5% by weight of water were continuously pumped at the rates of 62 and 560 kg/h, respectively. Under these conditions, a molar ratio of toluene/nitric acid was 1.68, a linear velocity in a static mixer was 1.04 m/sec, and a retention time in a static mixer was 2.5 sec. In a steady state one hour after initiation of the reaction, an inlet temperature was 82° C. and an outlet temperature was 130° C. Analysis of an acid phase of a reaction solution sampled at the outlet indicated that reactivity of nitric acid to input of nitric acid was 99%. Ratios of by-products to mononitrotoluenes were 950 ppm for dinitrotoluenes (DNTS) and 540 ppm for nitrocresols. Relative isomer ratios for mononitrotoluene were 55.3% for O-nitrotoluene, 4.8% for m-nitrotoluene and 39.9% for p-nitrotoluene.

COMPARATIVE EXAMPLE 1

In a 500 mL autoclave, 268 g of mixed acid consisting of 63.5% by weight of sulfuric acid, 5.2% by weight of nitric acid and 31.3% by weight of water was heated to 99° C.; then 22.4 g of benzene at 15° C. was added with pressure using nitrogen to raise the pressure in the system to $3 \times 10^5$ Pa(gage pressure); and the mixture was reacted at 600 rpm for 300 sec. Under these conditions, a molar ratio of benzene/nitric acid was 1.3 and an autoclave temperature rose to 140° C. Analysis of an acid phase of a reaction solution indicated that reactivity of nitric acid to input of nitric acid was 99%. Analysis of the organic phase indicated that ratios of by-products to nitrobenzene were 380 ppm for DNBS, 1500 ppm for DNPs and 1000 ppm for TNPS.

COMPARATIVE EXAMPLE 2

The procedure as described in Comparative Example 1 was carried out, except that chlorobenzene was heated in an autoclave and that 250 g of mixed acid consisting of 70% by weight of phosphoric acid, 5.2% by weight of nitric acid and 25.8% by weight of water was added with pressure. Under these conditions, a molar ratio of chlorobenzene/nitric acid was 3 and an autoclave temperature rose to 138° C. Analysis of an acid phase of a reaction solution indicated that reactivity of nitric acid to input of nitric acid was 99%. Analysis of the organic phase indicated that ratios of by-products to nitrochlorobenzene were 2400 ppm for DNCBs and 1000 ppm for CPs.

What is claimed is:

1. A process for preparing an aromatic mononitro compound comprising reacting a mixed acid containing nitric acid and an aromatic compound in a reactor comprised of a tube containing a plurality of twisted tabular members aligned in sequence so that a front margin of one twisted tabular member is substantially perpendicular to a back margin of a preceding member, followed by a hollow tube and followed by a tube containing a plurality of twisted tabular members aligned in sequence so that a front margin of one twisted tabular member is substantially perpendicular to a back margin of a preceding member.

2. The process of claim 1 wherein the twisted tabular members are made from ceramic material.

3. The process of claim 1 wherein the reaction is conducted in the reactor below 160° C.

4. The process of claim 1 wherein the mixed acid has a composition of 1 to 10% by weight of nitric acid, 20 to 40% by weight of water and the remainder of sulfuric acid and/or phosphoric acid.

5. The process of claim 1 wherein fluid in the reactor has a linear velocity of 20 to 300 cm/sec.

6. The process of claim 1 wherein the aromatic compound is selected from the group consisting of benzene, toluene, chlorobenzene, naphthalene and anthraquinone.

7. The process of claim 1 wherein a reaction mixture discharged from the reactor is separated into an acid phase and an organic phase, the acid phase is then subjected to flash evaporation to adjust its concentration and the resulting acid phase is then returned to the reactor for further reaction.

* * * * *

UNITED STATES PATENT AND TRADEMARK OFFICE
CERTIFICATE OF CORRECTION

PATENT NO. : 5,763,687
DATED : June 9, 1998
INVENTOR(S) : Jyoji MORISAKI, et al

It is certified that error appears in the above-identified patent and that said Letters Patent is hereby corrected as shown below:

On the title page, item [75]

amend the address of the third inventor to read: Kouki OOGAKI, Miike

Under the U.S. Patent Documents, please add the following 5,313,009   5/94    Guenkel et al
3,704,006   11/72   Grout et al Insert "OTHER DOCUMENTS" with the following information also cited by the Examiner:

Perry's Chemical Engineers' HandBook, Sixth Edition, pp. 19-22 - 19-23, 1984

Insert "PRIORITY INFORMATION" as follows:

December 15, 1995   [JP]   Japan ................................................. 7-326907
December 19, 1995   [JP]   Japan ................................................. 7-330052
December 26, 1995   [JP]   Japan ................................................. 7-339040

Signed and Sealed this

Twenty-seventh Day of April, 1999

Attest:

Attesting Officer

Q. TODD DICKINSON

Acting Commissioner of Patents and Trademarks